(12) United States Patent
Murata

(10) Patent No.: US 8,142,735 B2
(45) Date of Patent: *Mar. 27, 2012

(54) TEST APPARATUS

(75) Inventor: Yasuhito Murata, Kyoto (JP)

(73) Assignee: Arkray, Inc., Kyoto-shi, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/758,952

(22) Filed: Apr. 13, 2010

(65) Prior Publication Data

US 2010/0261264 A1 Oct. 14, 2010

Related U.S. Application Data

(63) Continuation of application No. 10/493,919, filed as application No. PCT/JP02/11229 on Oct. 29, 2002, now Pat. No. 7,749,439.

(30) Foreign Application Priority Data

Oct. 29, 2001 (JP) ................................. 2001-330336

(51) Int. Cl.
*G01N 21/75* (2006.01)
(52) U.S. Cl. ....................................................... 422/412
(58) Field of Classification Search ..................... 422/58, 422/412
See application file for complete search history.

(56) References Cited

U.S. PATENT DOCUMENTS

| | | | |
|---|---|---|---|
| 5,368,275 A | 11/1994 | Ketcham et al. | |
| 5,744,096 A | 4/1998 | Jones et al. | |
| 5,962,215 A * | 10/1999 | Douglas et al. | 435/4 |
| 5,972,187 A | 10/1999 | Parce et al. | |
| 6,001,307 A * | 12/1999 | Naka et al. | 422/81 |
| 6,008,056 A | 12/1999 | Thieme | |
| 6,204,375 B1 | 3/2001 | Lader | |
| 7,749,439 B2 * | 7/2010 | Murata | 422/410 |

FOREIGN PATENT DOCUMENTS

| | | |
|---|---|---|
| JP | 10-170510 | 6/1998 |
| JP | 10-332699 | 12/1998 |
| JP | 11-183475 | 7/1999 |
| JP | 2001-021556 | 1/2001 |
| WO | WO 88/06731 | 9/1988 |
| WO | WO 99/33559 | 7/1999 |
| WO | WO 9953322 A1 * | 10/1999 |
| WO | WO 01/51205 | 7/2001 |

* cited by examiner

*Primary Examiner* — Bobby Ramdhanie

(74) *Attorney, Agent, or Firm* — Knobbe, Martens, Olson & Bear, LLP

(57) ABSTRACT

A test apparatus is disclosed for measuring a component. The test apparatus maintains the amount of a specimen to be used for a reaction with a reagent at a constant value by allowing all of a fluid specimen to be measured and thus improves the accuracy and reproducibility of a test. The test apparatus includes a solution storage unit capable of holding a solution beforehand or allowing a solution to be filled therein, a capillary having a first end part and a second end part for storing the fluid specimen, and a test piece for measuring the component to be measured in the specimen. The solution storage unit and the second end part of the capillary are communicable with each other, and the first end part of the capillary is placed so as to be in contact with the test piece.

8 Claims, 5 Drawing Sheets

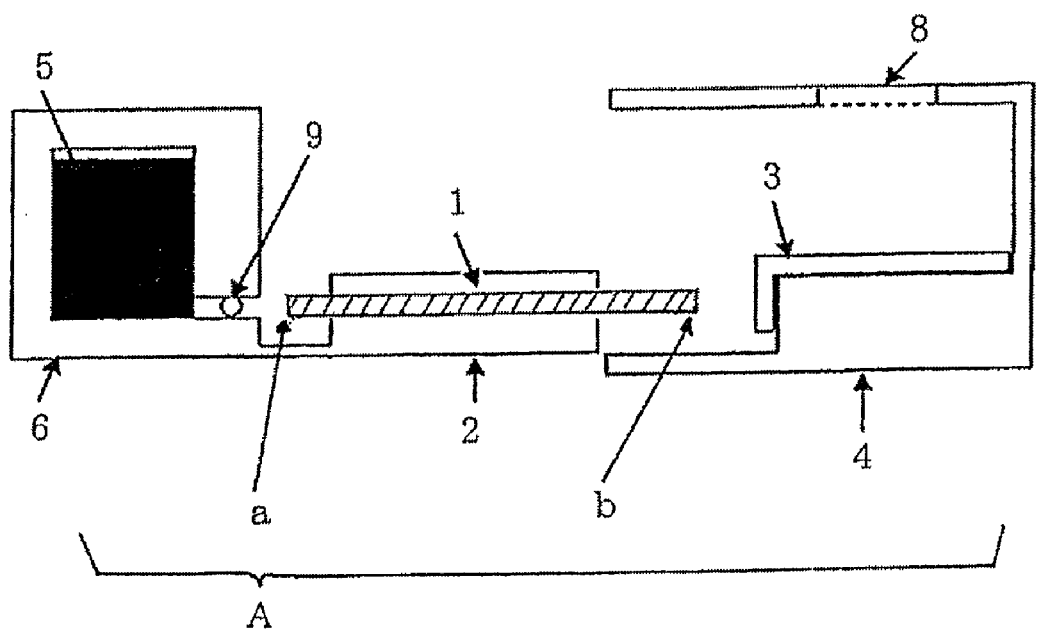
*Fig. 2a*
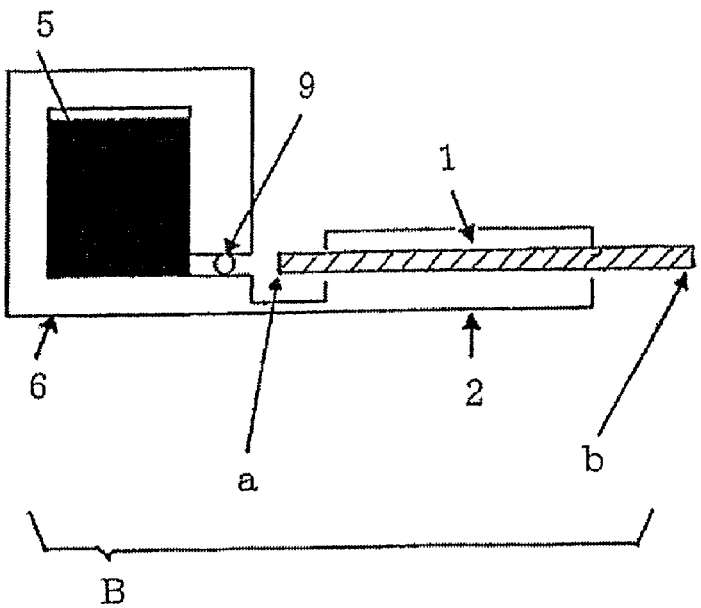
*Fig2. b*

TEST APPARATUS

RELATED APPLICATIONS

This application is a continuation of U.S. application Ser. No. 10/493,919, filed Apr. 27, 2004, now U.S. Pat. No. 7,749,439, issued Jul. 6, 2010, which is the U.S. National Phase under 35 U.S.C. §371 of International Application PCT/JP02/11229, filed Oct. 29, 2002, published in a non-English language, which claims priority of Japanese Patent Application No. 2001-330336, filed Oct. 29, 2001.

TECHNICAL FIELD

The present invention belongs to the technical field of chemical analysis, in particular to the technical field of immunoassay. Specifically, a test apparatus of the present invention is preferably intended to analyze biological materials.

BACKGROUND ART

Heretofore, various apparatuses for extracorporeal diagnosis have been studied as means of carrying out chemical analysis using a biological material.

Out of those, now under study is a test apparatus for detecting a component to be measured in a biological fluid by allowing a specimen collected by contacting a biological fluid specimen to react with a test piece for measuring the component and by detecting the reaction state of the test piece to measure the component.

Immunochromatography which is one solution developing method (chromatography) is a technique for detecting an immunocomplex formed from a component to be measured and a substance for this component on a reagent layer by using a labeled reagent.

To allow the above test piece to react with a specimen containing the component to be measured in this immunochromatography, various buffers are generally added as well.

The following methods are currently employed to diagnose a component to be measured using a test piece, specimen, and buffer.

The specimen is collected with a capillary and dropped on the test piece. After that, the buffer is dropped on the test piece. The reaction state of the test piece is detected.

However, in the above method, the specimen may adhere to and remain on the inner wall of the capillary at the time of dropping by the influence of the viscosity or the like of the specimen. In this case, not all of the collected specimen could be dropped on the test piece. That is, although the capacity of the specimen collected from a subject is constant, the amount of the specimen to be used for a reaction with the reagent is not constant, thereby causing problems with the accuracy and reproducibility of the test.

Therefore, a test method for a component to be measured and a test apparatus suitably used for the method in which all of a specimen in a capillary collected from a subject can be directly transferred onto a test piece to be used for a reaction with a reagent have been desired.

DISCLOSURE OF THE INVENTION

The present invention has been made in view of the above situation, and an object of the present invention is to provide a test apparatus for measuring a component to be measured, which can maintain the amount of a specimen to be used for a reaction with a reagent at a constant value and can improve the accuracy and reproducibility of a test by allowing all of a fluid specimen to be measured, specifically a biological fluid specimen to react with a test piece.

The inventor of the present invention has conducted intensive studies to solve the above problems and has found that a test apparatus for measuring a component to be measured in which the amount of a specimen to be used for a reaction with a reagent is made constant by using a solution can be provided (more specifically a buffer) for a reaction between a test piece and a specimen to wash away the specimen in a capillary. The present invention has been accomplished based on this finding.

That is, the present invention relates to:

(1) A test apparatus for measuring a component to be measured in a fluid specimen, comprising:

a solution storage unit capable of holding a solution beforehand or allowing a solution to be filled therein;

a capillary having a first end part and a second end part for storing the fluid specimen;

a test piece for measuring the component to be measured in the specimen, wherein the solution storage unit and the second end part of the capillary are communicable with each other, and the first end part of the capillary is placed so as to bring into contact with the test piece.

(2) The test apparatus according to item (1), wherein when the solution in the solution storage unit is communicated with the second end part of the capillary and the first end part of the capillary is brought into contact with the test piece, the specimen is forced out by the solution to be applied to the test piece.

(3) The test apparatus according to item (1) or (2), wherein the fluid specimen is a biological fluid specimen.

(4) The test apparatus according to any one of items (1) to (3), wherein the capillary storing the fluid specimen is obtained by bringing an end part of the capillary into contact with the fluid specimen to collect the specimen.

(5) The test apparatus according to any one of items (1) to (3), wherein the capillary storing the fluid specimen is obtained by supplying the fluid specimen from a specimen feed unit provided separately in the test apparatus and injecting the specimen into the capillary.

(6) The test apparatus according to item (1) or (2), wherein the solution storage unit and the capillary are separated from each other by a film, the capillary is provided to be movable toward the film, and when the capillary is moved toward the film, the second end part of the capillary makes a hole in the film to communicate the solution in the solution storage unit with the specimen in the capillary.

(7) The test apparatus according to item (1) or (2), wherein the solution storage unit and the capillary are connected to each other by a tube the inside of which is blocked with a ball, the capillary is provided to be movable toward the solution storage unit, and when the capillary is moved toward the solution storage unit and the ball is pushed by the second end part of the capillary, the ball is forced out into the solution storage unit from the tube to communicate the solution in the solution storage unit with the specimen in the capillary.

(8) The test apparatus according to item (1) or (2), wherein the solution storage unit and the capillary are communicated with each other beforehand, and when the solution is injected into the solution storage unit, the solution in the solution storage unit and the specimen in the capillary are communicated with each other.

(9) A sampling tool used in the test apparatus according to item (1), comprising:
a solution storage unit holding a solution beforehand; and
a capillary having a first end part and a second end part for storing a fluid specimen, wherein
the solution storage unit and the capillary are separated from each other by a film, the capillary is provided to be movable toward the film, and the solution storage unit and the capillary are arranged such that when the capillary is moved toward the film, the second end part of the capillary makes a hole in the film to communicate the solution in the solution storage unit with the specimen in the capillary.

(10) A sampling tool used in the test apparatus according to item (1), comprising:
a solution storage unit holding a solution beforehand; and
a capillary having a first end part and a second end part for storing a fluid specimen, wherein
the solution storage unit and the capillary are connected to each other by a tube the inside of which is blocked with a ball, the capillary is provided to be movable toward the solution storage unit, and the solution storage unit and the capillary are arranged such that when the capillary is moved toward the solution storage unit and the ball is pushed by the second end part of the capillary, the ball is forced out into the solution storage unit from the tube to communicate the solution in the solution storage unit with the specimen in the capillary.

The present invention will be described in detail hereinunder.

The test apparatus of the present invention is a test apparatus for measuring a component to be measured in a fluid, specifically a biological fluid.

Although the fluid is preferably a biological fluid, it may be river water or ground water as long as a component to be measured in the river water or ground water can be measured with an immune reaction. The term "biological fluid" as used herein means a fluid derived from a living creature such as a human being, for example, blood, blood plasma, serum or fraction thereof, or, urine. The component to be measured is not particularly limited as long as it can be measured with a test piece. For example, the component to be measured is a component in a biological fluid, as exemplified by a protein such as an enzyme, antigen, or antibody, a sugar, a lipid, a low molecular weight substance, or a microorganism such as a virus or bacterium. The component to be measured may be a component in river water or ground water, as exemplified by an environmental hormone such as dioxin or PCB, or residual agricultural chemicals in food.

The test apparatus of the present invention includes at least a solution storage unit, a capillary, and a test piece.

Since the solution storage unit is used to inject a solution into the test apparatus, the solution storage unit may or may not hold the solution beforehand as long as the solution can be injected into the solution storage unit before use. In the present invention, the solution is suitably selected according to the types of a fluid specimen and a test piece used, but is particularly preferably a buffer when a biological fluid specimen is used. Therefore, in the following description, the solution may be replaced with a buffer as a more specific example thereof. For example, the solution storage unit may also be referred to as "buffer storage unit".

The capillary is used to contain a fluid specimen. The capillary has a first end part and a second end part.

To install the capillary containing the fluid specimen in the test apparatus, the capillary is installed in the test apparatus after the fluid specimen is injected into the capillary, or the fluid specimen is injected into the capillary after the capillary is installed in the test apparatus. Both methods may be employed.

The above specific method will be described hereinbelow, taking a biological fluid specimen as an example.

An end part of the capillary is brought into contact with the biological fluid specimen to collect the specimen to thereby obtain the capillary containing the biological fluid specimen, and then the capillary containing the biological fluid specimen is installed at a predetermined position of the test apparatus.

Alternatively, the biological fluid specimen is supplied into the capillary installed in the test apparatus from a specimen feed unit provided separately in the test apparatus to be injected into the capillary.

Capillary action is utilized as a simple method of storing the fluid specimen (preferably a biological fluid specimen) in the above capillary. More specifically, when the capillary is brought into contact with the fluid specimen, the specimen is absorbed into the capillary by capillary action. When a capillary having a suitable shape is used and an end part opposite to the specimen side of the capillary is opened, the capillary is filled with the specimen. Therefore, a predetermined amount of the specimen can be collected.

The test piece is not limited by a specific principle and method as long as a component to be measured in the fluid specimen can be measured, and a test piece which is generally used may be used.

More specifically, for instance, if the test piece contains a reagent which reacts with the component to be measured, when the specimen containing the component to be measured is spread over a reagent layer on the test piece, the component reacts with the reagent. The presence or absence of the component can be known by detecting the presence or absence of this reaction. Immunochromatographic paper may be used as the test piece.

The test apparatus of the present invention includes the above solution storage unit, capillary, and test piece, the second end part of the capillary is placed to be communicable with the solution storage unit, and the first end part of the capillary is placed so as to come into contact with the test piece.

In the above test apparatus, when the solution in the solution storage unit and the second end part of the capillary are communicated with each other, and the first end part of the capillary is brought into contact with the test piece, the specimen is forced out by the solution to be applied to the test piece.

A test apparatus according to a first aspect of the present invention is structured such that the solution storage unit and the capillary are separated from each other by a film, the capillary is provided to be movable toward the film, and when the capillary is moved toward the film, the second end part of the capillary makes a hole in the film to communicate the solution in the solution storage unit with the specimen in the capillary.

Since the above film may be formed of a member which can be physically broken, for example, it is formed on the wall of the solution storage unit, and a hole can be made by pushing the film with the capillary, specifically, an aluminum laminate film or the like may be used as the film.

A test apparatus according to a second aspect of the present invention is structured such that the solution storage unit and the capillary are connected to each other by a tube the inside of which is blocked with a ball, the capillary is provided to be movable toward the solution storage unit, and the solution storage unit and the capillary are arranged such that when the capillary is moved toward the solution storage unit and the ball is pushed by the second end part of the capillary, the ball is forced out into the solution storage unit from the tube to communicate the solution in the solution storage unit with the specimen in the capillary.

The above ball is a bead or the like.

According to a third aspect of a test apparatus of the present invention, the test apparatus is structured such that the above solution storage unit and the capillary are communicated with each other beforehand, and when the solution is injected into the solution storage unit, the solution in the solution storage unit and the specimen in the capillary are communicated with each other. When this test apparatus is used, the solution can be injected at any time without storing the solution in the solution storage unit beforehand.

BRIEF DESCRIPTION OF THE DRAWINGS

FIG. 2(a) is a schematic diagram of a test apparatus according to another embodiment of the present invention.

FIG. 2(b) is a schematic diagram of a specimen collecting tool having a buffer according to the above embodiment of the present invention.

BEST MODE FOR CARRYING OUT THE INVENTION

Figure 1A:
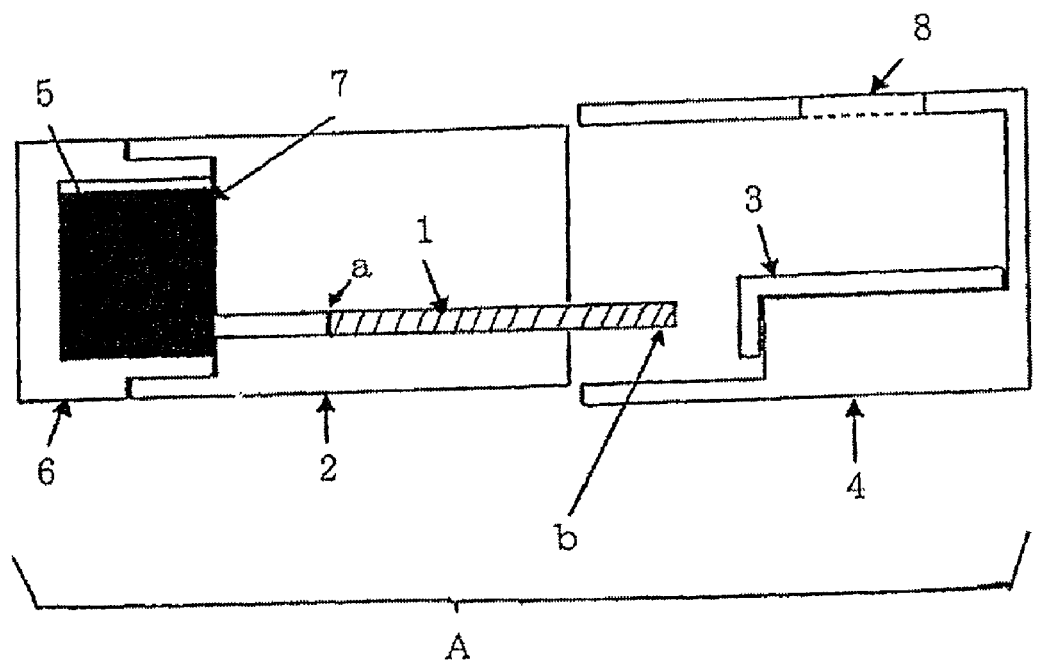
FIG. 1(a) is a schematic diagram of a test apparatus according to an embodiment of the present invention.

A test apparatus according to a first embodiment of the present invention will be described with reference to FIG. 1.

A case where the fluid specimen is a biological fluid specimen will be specifically described as a preferred embodiment of the present invention.

This embodiment is a test apparatus (A) having a buffer storage unit (6) which holds a buffer (5) and is sealed up with an aluminum laminate film (7).

The test apparatus shown in FIG. 1 has a sampling tool support unit (2) for supporting a capillary (1).

The test apparatus also has a test piece support unit (4) for supporting a test piece (3).

Reference numeral 8 in FIG. 1 denotes a measurement window. When the state of the test piece after it reacts with a component to be measured is observed through the measurement window, the presence or absence of a reaction can be known from the outside of the apparatus while the test piece is held in the apparatus without taking it out from the apparatus.

In the test apparatus shown in FIG. 1, the test piece (3), the capillary (1), and the buffer storage unit (6) are detachable from the apparatus.

The sampling tool support unit (2) and the test piece support unit (4) can be placed at or moved to the respective desired positions.

The test procedure using the test apparatus shown in FIG. 1(a) will be described hereinunder.

A specimen is collected from a subject using the capillary. Stated more specifically, the first end part of the capillary is brought into contact with a biological fluid specimen to collect the specimen.

The capillary containing the specimen is arranged such that the buffer storage unit (6) and the second end part (a) of the capillary become communicable with each other.

Stated more specifically, the capillary (1) is placed adjacent to the buffer storage unit (6). The capillary may be inserted into the sampling tool support unit after the support unit is installed, or the sampling tool support unit may be placed adjacent to the buffer storage unit after the capillary is inserted into the support unit.

The first end part (b) of the capillary and the test piece (3) are arranged such that they can contact each other.

Stated more specifically, the test piece (3) is placed adjacent to the capillary (1). The test piece (3) may be inserted into the test piece support unit after the support unit is installed, or the test piece support unit may be placed adjacent to the sampling tool support unit in which the capillary is placed after the test piece is inserted into the test piece support unit.

The buffer in the buffer storage unit and the second end part of the capillary are communicated with each other. With this arrangement, when the first end part of the capillary is brought into contact with the test piece, the specimen is forced out by the buffer and applied to the test piece.

The buffer and the second end part of the capillary are communicated with each other as follows.

The buffer storage unit and the capillary are separated by a film as shown in FIG. 1. Then, when the capillary is moved toward the film (the capillary itself may be moved or the sampling tool support unit may be moved), the second end part of the capillary makes a hole in the film so that the buffer in the buffer storage unit and the specimen in the capillary can be communicated with each other.

By this communication, the buffer passes through the hole formed in the film, goes through the capillary, and is discharged to the outside of the tube from the first end part together with the specimen in the capillary. The buffer and the specimen reach the test piece, and the component to be measured in the specimen is spread over the reagent layer on the test piece. At this time, the position of the test piece can be suitably adjusted by moving the test piece support unit.

Once all the specimen in the capillary is applied to the test piece, a predetermined amount of the specimen can be always used for a reaction with the reagent.

In the above apparatus, the penetration of the buffer into the capillary is utilized in order for the buffer to force out the specimen from the capillary. An air hole or pressure supply means for applying arbitrary pressure to the buffer may be optionally provided separately in the test apparatus at a desired position of the buffer storage unit.

A test apparatus according to a second embodiment of the present invention will be described with reference to FIG. 2. This embodiment is a test apparatus (A) having a buffer storage unit (6) which holds the buffer (5) beforehand and is sealed up with a bead (9). FIG. 2 differ from FIG. 1 in communication between the buffer in the buffer storage unit and the second end part of the capillary.

The buffer storage unit and the capillary are connected to each other by a pipe the inside of which is blocked with the bead (9) as shown in FIG. 2. When the capillary is moved toward the buffer storage unit (the capillary itself may be moved, or the sampling tool support unit may be moved) to push the bead with the second end part of the capillary, the bead is forced out into the buffer storage unit from the tube, whereby the buffer in the buffer storage unit and the specimen in the capillary can be communicated with each other.

Except the above, this test apparatus is the same as the apparatus shown in FIG. 1 in constitution and operation.

Figure 3:
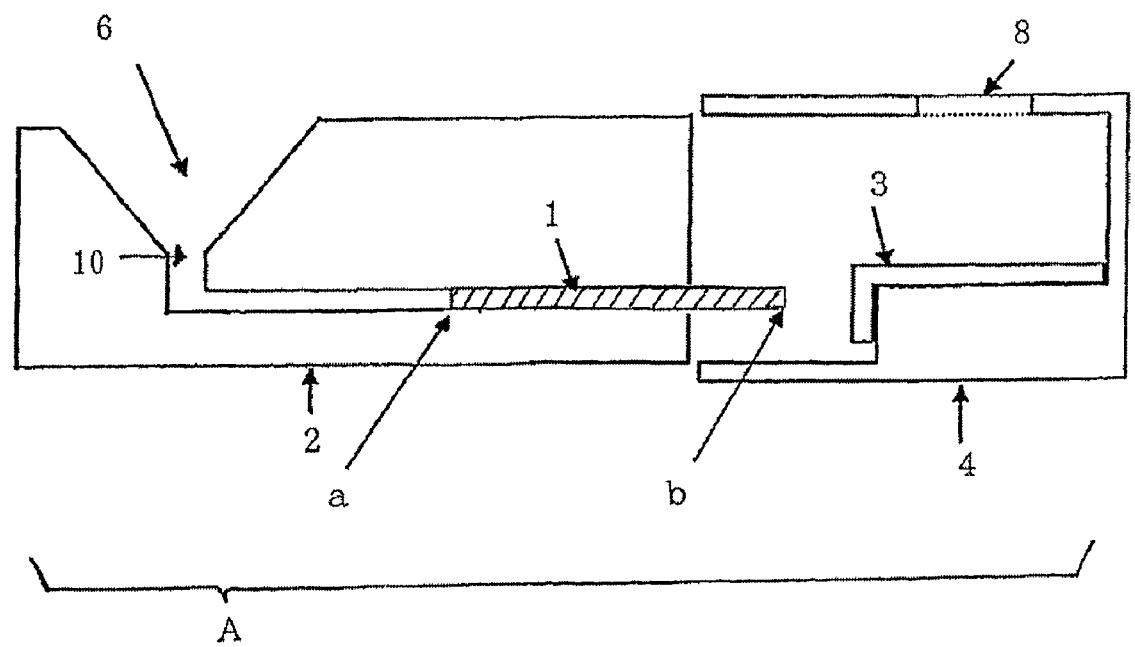
FIG. 3 is a schematic diagram of a test apparatus according to still another embodiment of the present invention.

A test apparatus according to a third embodiment of the present invention will be described with reference to FIG. 3. This embodiment is a test apparatus (A) in which the buffer (5) is not stored beforehand but is supplied into the buffer storage unit (6) as required and injected from a buffer injection port (10) into the capillary (1). FIG. 3 differs from FIG. 1 and FIG. 2 in communication between the buffer and the second end part of the capillary.

The buffer storage unit and the capillary are communicated with each other beforehand as shown in FIG. 3. When the buffer is injected into the buffer storage unit, the buffer in the buffer storage unit and the specimen in the capillary can be communicated with each other. Stated more specifically, a flow passage through which the buffer passes is formed between the buffer injection port and the second end part of the capillary in the test apparatus of FIG. 3. The flow passage has a structure in which the buffer flows from the above buffer injection port toward the capillary. In the test apparatus having this structure, the buffer can be injected into the buffer storage unit when desired without storing the buffer in the buffer storage unit beforehand as shown in FIG. 1 or FIG. 2.

Except the above, this test apparatus is the same as the apparatus shown in FIG. 1 in constitution and operation.

A test apparatus according to another embodiment of the present invention will be described hereinunder. The embodiment described below differs from the embodiments described with reference to FIGS. 1 to 3 in how a biological fluid specimen is stored in the capillary.

The test apparatus according to the fourth embodiment of the present invention will be described with reference to FIG. 4. In this embodiment, a specimen feed unit (11) is provided in the test apparatus separately.

A biological fluid specimen (12) is supplied from this specimen feed unit into the capillary (1) installed in the test apparatus. With this arrangement, after the capillary is installed in the test apparatus, the specimen can be stored in the capillary when desired without storing the specimen in the capillary before installing the capillary in the test apparatus.

To inject the biological fluid specimen supplied from the specimen feed unit into the capillary, a film (13) may be positively provided as shown in FIG. 4. This film is made of a member which can be physically broken. For instance, a hole can be made by pushing the film with the capillary. Therefore, specific examples thereof include an aluminum laminate film.

Depending on the designs of the specimen feed unit, capillary, tube in the sampling tool support unit into which the capillary is inserted, and the like, the film (13) may not be provided.

To inject the specimen supplied from the specimen feed unit into the capillary, capillary action may be utilized. Suction means (not shown) for injecting the specimen into the capillary may be positively provided as required.

Figure 4A:
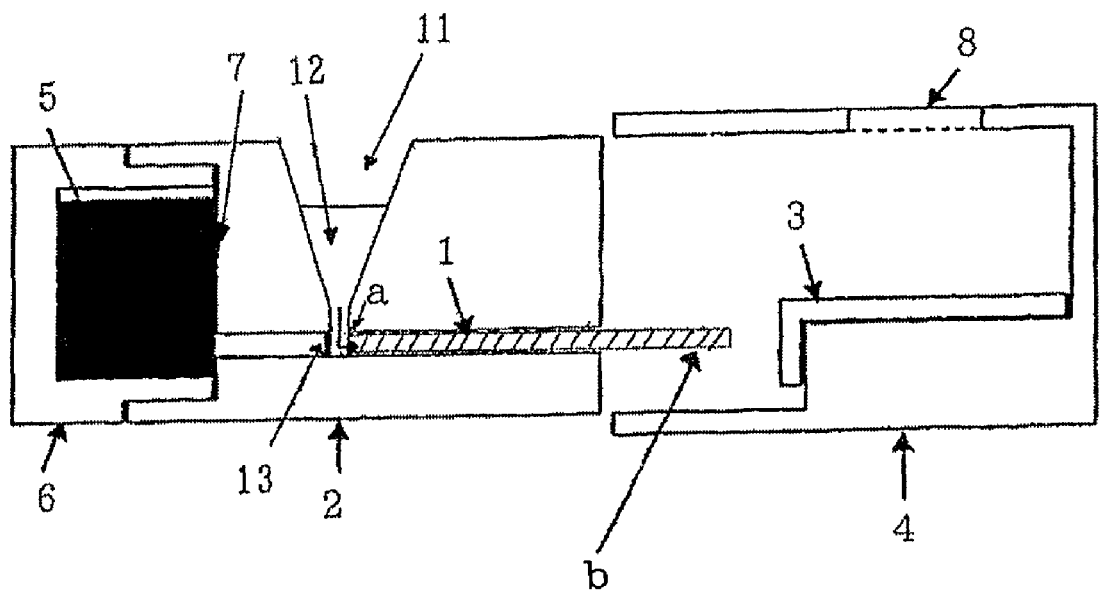
FIG. 4(a) is a schematic diagram of a test apparatus according to a further embodiment of the present invention.
Figure 4B:
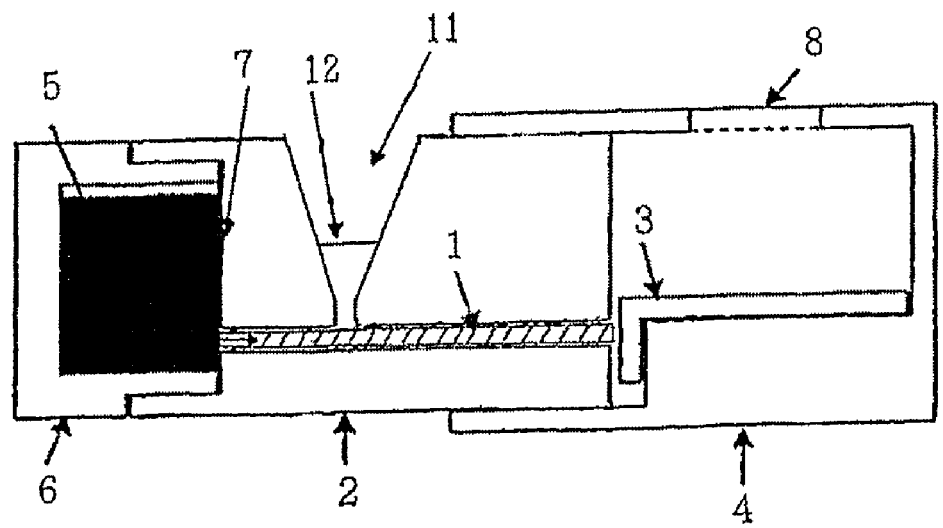
FIG. 4(b) is a schematic diagram of the test apparatus shown in FIG. 4(a) after the position of a capillary has been moved.

FIG. 4(b) shows that the buffer in the buffer storage unit and the specimen in the capillary are communicated with each other by moving the capillary after supplying and injecting the biological fluid specimen (12) into the capillary (1) in the test apparatus shown in FIG. 4(a).

Except the above, this apparatus is the same as the apparatus shown in FIG. 1 in constitution and operation.

A test apparatus according to a fifth embodiment of the present invention will be described with reference to FIG. 5. In this embodiment, the specimen feed unit (11) is provided in the test apparatus separately like the apparatus shown in FIG. 4.

The description of the specimen feed unit (11) is the same as that shown in FIG. 4.

Figure 5A:
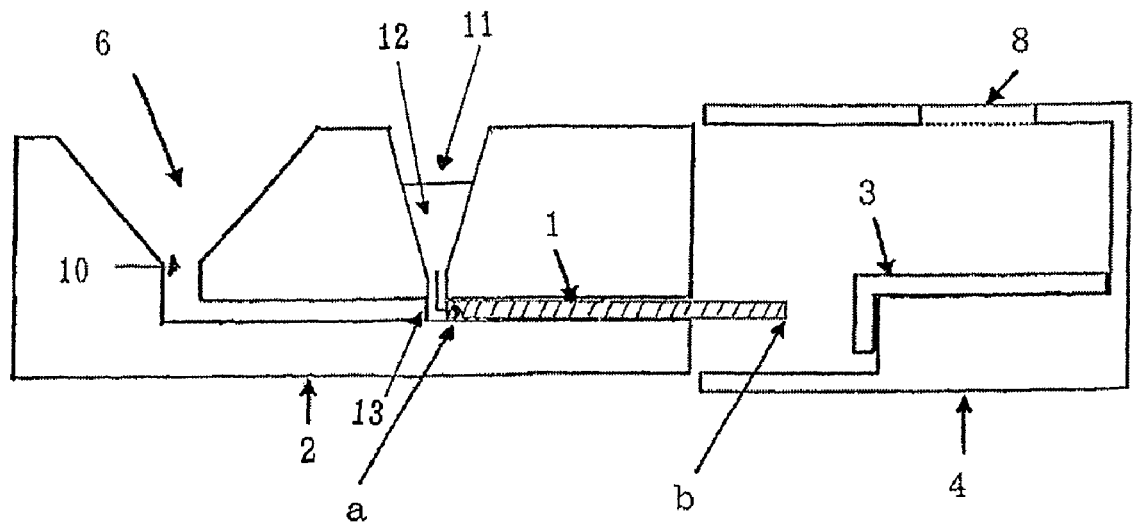
FIG. 5(a) is a schematic diagram of a test apparatus according to a still further embodiment of the present invention.
Figure 5B:
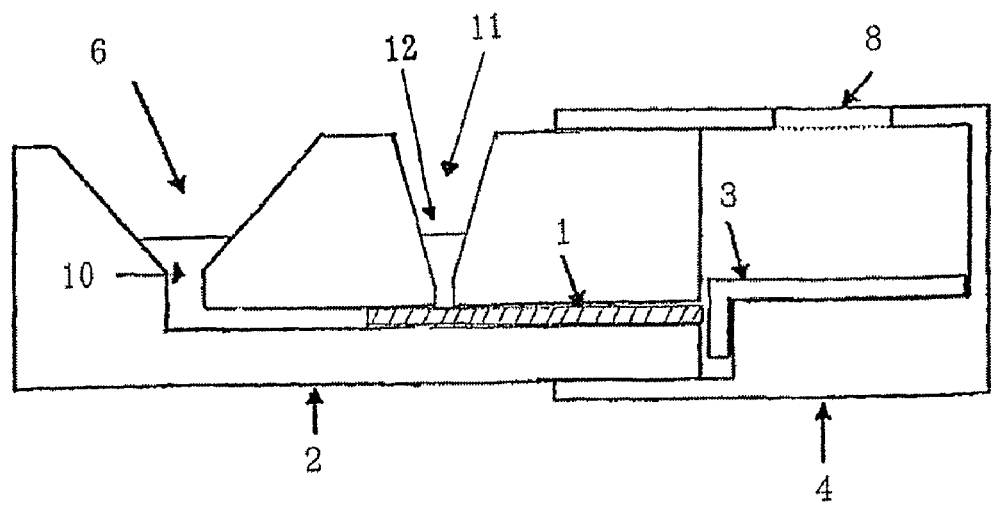
FIG. 5(b) is a schematic diagram of the test apparatus shown in FIG. 5(a) after the position of the capillary has been moved.

FIG. 5(b) shows that the capillary (1) is moved after the biological fluid specimen (12) is supplied and injected into the capillary in the test apparatus shown in FIG. 5(a). When the buffer is supplied into the buffer storage unit in the state shown in FIG. 5(b), the buffer in the buffer storage unit and the specimen in the capillary can be communicated with each other.

Except the above, this apparatus is the same as the apparatus shown in FIG. 3 in constitution and operation.

The present invention provides a sampling tool having a buffer which can be used in the above test apparatus.

Figure 1B:
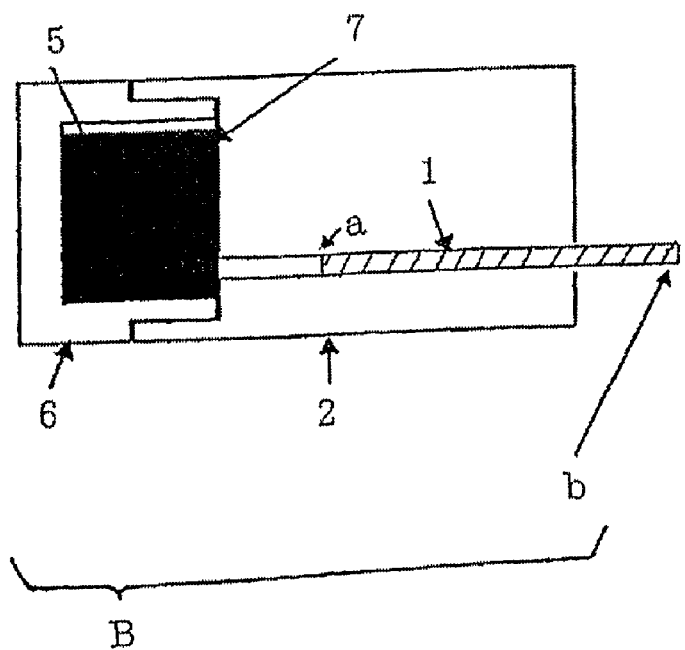
FIG. 1(b) is a schematic diagram of a specimen collecting tool having a buffer according to the above embodiment of the present invention.

More specifically, the sampling tool of the present invention corresponds to a part (B) shown in FIG. 1(b) in the case of the test apparatus shown in FIG. 1(a) and to a part (B) shown in FIG. 2(b) in the case of the test apparatus shown in FIG. 2(a).

That is, the sampling tool of the present invention is a sampling tool comprising:

a solution storage unit holding a solution (preferably, buffer) beforehand; and a capillary having a first end part and a second end part for storing a fluid specimen (preferably, biological fluid specimen), wherein the solution storage unit and the capillary are separated from each other by a film, the capillary is provided to be movable toward the film, and the solution storage unit and the capillary are arranged such that when the capillary is moved toward the film, the second end part of the capillary makes a hole in the film to communicate the solution in the solution storage unit with the specimen in the capillary.

Moreover, the sampling tool of the present invention is a sampling tool comprising:

a solution storage unit holding a solution (preferably, buffer) beforehand; and a capillary having a first end part and a second end part for storing a fluid specimen (preferably, biological fluid specimen), wherein the solution storage unit and the capillary are connected to each other by a tube the inside of which is blocked with a ball, the capillary is provided to be movable toward the solution storage unit, and the solution storage unit and the capillary are arranged such that when the capillary is moved toward the solution storage unit and the ball is pushed by the second end part of the capillary, the ball is forced out into the solution storage unit from the tube to communicate the solution in the solution storage unit with the specimen in the capillary.

In the present invention, a reaction between the reagent and the component to be measured includes a biologically specific reaction such as a reaction between an enzyme and a matrix, a reaction between an antigen and an antibody, a reaction between a sugar chain and lectin, or a reaction between a ligand and a receptor.

Diagnosis using the test apparatus of the present invention can be used for the analysis of a trace substance in a biological fluid such as blood or urine when a component to be measured and a reagent are suitably selected.

The above test apparatus of the present invention can be used not only when the fluid specimen is a biological fluid specimen but also when the fluid specimen is another fluid specimen. Specifically, the test apparatus of the present invention can be used to detect environmental hormones such as dioxin and PCB in river water and ground water and the residual agricultural chemicals in food by an immune reaction.

The method of detecting a component to be measured is not particularly limited as long as a reaction between the above reagent and the component to be measured can be detected with the method. The method is, for example, one in which a component to be measured is detected from an optical change caused by a reaction between the above reagent and the component, or one in which a component to be measured is detected from an electrochemical change caused by a reaction between the above reagent and the component. When a reagent which quantitatively reacts with the component to be measured is used as the above reagent in each of those methods of detecting a component to be measured, the component is detected, and at the same time, the amount of the component can be determined by measuring an optical change, electrochemical change, or the like.

In the method of detecting a component to be measured from an optical change, the optical change is generally a color development reaction caused by a reaction between the component and the above reagent. The optical change is not only color development but also discoloration, fluorescence, emission, or the like. To determine the amount of the component, for example, the measurement of the above optical change using an absorptiometer or fluorophotometer, or Raman spectrometry all of which are commonly used may be employed.

In the present invention, the types of the component to be measured, reagent, and solution may be suitably determined in consideration of the above analytical purpose and detection method, and various combinations of these can be selected.

In the present invention, any fluid specimen is acceptable as long as it is generally measured by immunochromatography. For example, blood can be collected from a subject. The amount of the specimen collected by using a capillary is 0.1 to 100 µl, preferably 0.1 to 10 µl.

Any test piece is acceptable as long as it is commonly used in immunochromatography. The term "immunochromatography" used herein means a method of detecting a component to be measured by allowing the component in the specimen to react with a marker in a first region on the test piece to form an immunocomplex, moving the immunocomplex over the test piece, allowing an antibody immobilized in a second region to react with the immunocomplex, and observing a change at a reaction site by making use of a phenomenon that the marker remains at the reaction site of the test piece. Then, a desired test piece is obtained by selecting a marker and immobilized antibody to suit this principle. The film (material of the test piece) for holding the marker and immobilized antibody may be a porous film, more specifically a nitrocellulose film is preferably used. Items to be detected using immunochromatography include CRP, ASO, and IgG.

The solution is not particularly limited by the type of a material as far as it has the function of forcing out the specimen in the capillary. Any solution which is commonly used in general immunochromatography may be used. For example, a preferred example of the buffer which is preferably used as the solution is physiological saline. The amount of the buffer to be used is 10 to 50 µl, preferably 10 to 30 µl.

The following examples are provided to further illustrate the present invention.

Example 1

In FIG. 1, physiological saline was used as a solution (buffer). The buffer was in the buffer storage unit in an amount of 30 µl.

Blood as a specimen was collected by making a puncture in a finger of a subject with a lancet device. 10 µl of the fluid specimen was in the capillary.

A predetermined test piece was used to enable the detection of CRP (C reactive protein) as the component to be measured.

The above members were inserted into the apparatus of FIG. 1. The capillary was moved to break an aluminum laminate film on the side of the buffer storage unit so as to make a hole in the film.

The buffer entered the capillary, the specimen in the capillary was forced out, and the specimen and the buffer were developed over the test piece. The reaction of the test piece was observed.

As a result, a color development reaction was observed through the measurement window.

When this diagnosis was repeated 10 times, the same reaction result was observed and there was no variation in the reaction result. Therefore, it could be confirmed that highly reliable diagnosis could be made.

INDUSTRIAL APPLICABILITY

According to the present invention, all of a specimen can be applied on a test piece, and thus the amount of a specimen to be used for a reaction with a reagent can be regulated at a constant value. Accordingly, the present invention can provide a test apparatus for measuring a component to be measured, which can improve the accuracy and reproducibility of a test.

What is claimed is:

1. A test apparatus for measuring a component to be measured in a fluid specimen, comprising: a solution storage unit capable of holding a solution beforehand or allowing a solution to be filled therein; a capillary having a first end part and a second end part for storing the fluid specimen wherein the capillary storing the fluid specimen is adapted to obtain the fluid specimen by bringing the end part of the capillary into contact with the fluid specimen to collect the specimen; a test piece for measuring the component to be measured in the specimen, wherein the test piece contains a reagent which reacts with the component to be measured in the specimen and the component is reacted with the reagent and detected on the test piece, and wherein the solution storage unit and the second end part of the capillary are communicable with each other, and the first end part of the capillary is placed so as to bring into contact with the test piece, and wherein when the solution in the solution storage unit is communicated with the second end part of the capillary, and are separated from each other by a film, the first end part of the capillary is opened, and when the first end part of the capillary is brought into contact with the test piece, the specimen is forced out by the solution to be applied to the test piece.

2. The test apparatus according to claim 1, wherein the fluid specimen is a biological fluid specimen.

3. The test apparatus according to claim 1, wherein the capillary storing the fluid specimen is obtained by supplying the fluid specimen from a specimen feed unit provided separately in the test apparatus and injecting the specimen into the capillary.

4. The test apparatus according to claim 1, wherein the solution storage unit and the capillary are separated from each other by a film, the capillary is provided to be movable toward the film, and when the capillary is moved toward the film, the second end part of the capillary makes a hole in the film to communicate the solution in the solution storage unit with the specimen in the capillary.

5. The test apparatus according to claim 1, wherein the solution storage unit and the capillary are communicated with each other beforehand, and when the solution is injected into the solution storage unit, the solution in the solution storage unit and the specimen in the capillary are communicated with each other.

6. A sampling tool used in the test apparatus according to claim 1, comprising:
   a solution storage unit holding a solution beforehand; and
   a capillary having a first end part and a second end part for storing a fluid specimen, wherein
   the solution storage unit and the capillary are separated from each other by a film, the capillary is provided to be movable toward the film, and the solution storage unit and the capillary are arranged such that when the capillary is moved toward the film, the second end part of the capillary makes a hole in the film to communicate the solution in the solution storage unit with the specimen in the capillary.

7. A sampling tool used in the test apparatus according to claim 1, comprising:
   a solution storage unit holding a solution beforehand; and
   a capillary having a first end part and a second end part for storing a fluid specimen, wherein
   the solution storage unit and the capillary are connected to each other by a tube the inside of which is blocked with a ball, the capillary is provided to be movable toward the solution storage unit, and the solution storage unit and the capillary are arranged such that when the capillary is moved toward the solution storage unit and the ball is pushed by the second end part of the capillary, the ball is forced out into the solution storage unit from the tube to communicate the solution in the solution storage unit with the specimen in the capillary.

8. The test apparatus according to claim 1, wherein the test piece comprises at least one component selected from the group consisting of a marker, antibody, enzyme and reagent.

* * * * *